United States Patent
Piombini et al.

(10) Patent No.: US 7,773,208 B2
(45) Date of Patent: Aug. 10, 2010

(54) DEVICE AND PROCESS FOR MEASURING THE CHARACTERISATION BY REFLECTOMETRY

(75) Inventors: Herve Piombini, Esures sur Indre (FR); Philippe Voarino, Tours (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 12/302,793

(22) PCT Filed: May 29, 2007

(86) PCT No.: PCT/EP2007/055158

§ 371 (c)(1), (2), (4) Date: Nov. 26, 2008

(87) PCT Pub. No.: WO2007/138032

PCT Pub. Date: Dec. 6, 2007

(65) Prior Publication Data

US 2009/0116022 A1    May 7, 2009

(30) Foreign Application Priority Data

May 30, 2006 (FR) .................................. 06 51951

(51) Int. Cl.
*G01N 21/00*  (2006.01)
(52) U.S. Cl. .................... 356/237.1; 356/417; 356/445; 250/216; 250/458.1
(58) Field of Classification Search ... 356/237.1–237.6, 356/417, 445; 350/458.1, 216
See application file for complete search history.

(56) References Cited

U.S. PATENT DOCUMENTS

| 5,747,813 | A | 5/1998 | Norton et al. |
| 7,298,496 | B2 * | 11/2007 | Hill .......................... 356/237.2 |
| 2003/0071994 | A1 | 4/2003 | Borden et al. |
| 2009/0015831 | A1 * | 1/2009 | Yguerabide et al. ......... 356/337 |

OTHER PUBLICATIONS

D. Enard et al., "Universal spectrophotometer for determining the efficiency of optical components and systems," Applied Optics, Dec. 15, 1982, pp. 4459-4464, vol. 21, No. 24, Optical Society of America.
Patrick Bouchareine, "Spectrometrie Optique," Les Techniques de l'Ingenieur, Traite Mesures et Controle, R6310, pp. 1-31, Oct. 1994.
PCT International Search Report and Written Opinion for PCT/EP2007/055158 dated Jul. 19, 2007.
English Translation of the PCT Written Opinion of the International Searching Authority for PCT/EP2007/055158.

* cited by examiner

*Primary Examiner*—Gregory J Toatley, Jr.
*Assistant Examiner*—Iyabo S Alli
(74) *Attorney, Agent, or Firm*—Nixon Peabody LLP (57) ABSTRACT

Embodiments relate to a device for measuring characterisation by reflectometry including a source that emits a light beam, a detector, optics for processing and controlling this light beam so as to focus it on a reflective surface to be measured in the form of a spot and to receive it on the detector, command and acquisition modules, a camera and modules for imaging the spot on the detector and on the camera, wherein the camera is connected to the command and acquisition means so as to automatically focus the spot on the reflective surface to be measured and to automatically conjugate the reflective surface to be measured with the surface of the detector.

14 Claims, 6 Drawing Sheets

DEVICE AND PROCESS FOR MEASURING THE CHARACTERISATION BY REFLECTOMETRY

This application is a national phase of International Application No. PCT/EP2007/055158, entitled "DEVICE AND METHOD FOR MEASURING THE CHARACTERIZATION OF REFLECTOMETRY", which was filed on May 29, 2007, and which claims priority of French Patent Application No. 06 51951, filed May 30, 2006.

TECHNICAL FIELD

The invention relates to a device and a process for measuring characterisation by reflectometry.

PRIOR ART

As described in the document referenced [1] at the end of the description, spectrometry is the study of the distribution of amplitude or power (square of the amplitude) of a quantity as a function of frequency. In optics, the term "spectrometry" more specifically designates all of the instrumental techniques for analysing spectral power density, while spectroscopy is instead the science of spectra (atomic and molecular spectroscopy).

The formidable amount of information contained in an optical spectrum at medium or high resolution, associated with recent advances made in the construction of spectrometers and their automation, makes optical spectrometry a technique with numerous applications, from chemical engineering process tests to biomedical analyses, as well as environmental monitoring or operational monitoring of an electric ignition engine.

The term "spectrophotometer" is a term used by chemists and vendors of spectrometers. This is the term we will use below.

At present, commercial spectrophotometers are apparatuses that are conventionally used in transmission with good precision but with lower precision in reflection. For certain applications, in particular for opaque materials, it is necessary to know the reflection coefficient with good precision. In this specific case, the precisions obtained with such an apparatus by the National Physical Laboratory (UK) on aluminium samples (calibration certificate) are ±0.5% on [340-740 nm] and ±1.1% on [740-850 nm] at 2 σ, σ being the standard deviation of the signal measured.

There are various ways to measure the flux reflected, whether it is specular or diffuse (use of an integrating sphere), either spectrally (conventional spectrophotometers), or temporally (Fourier transform spectrometers).

In the case of a specular reflected flux, which is the case of the invention, the reflection is generally obtained by a modification of the optical path of the measuring channel in order to introduce the sample to be measured.

In this case, the sample supports do not have the mechanical rigidity necessary for good repositioning, and the surface of the light spot on the sample is several dozen mm², which causes an overall measurement capable of leading to an imprecise measurement if the sample is not perfectly planar.

The document referenced [2] at the end of the description describes a spectrophotometer that was developed to measure the absolute reflectance or transmittance of optical elements or systems.

In this spectrophotometer, a monochromatic beam, generated by a lamp and a monochromator, is divided by a beam separator. The beam transmitted and the beam reflected are directed toward a rotary disk with slots that cuts the two beams with two different frequencies. The measuring beam, which is the beam transmitted by the separator, and the reference beam, which is the beam reflected by the separator, are reflected in return by mirrors. The sample to be tested is placed in the measuring beam. The reflected part of the return measuring beam and the transmitted part of the return reference beam are combined again and directed toward a detector.

This spectrophotometer enables measurements close to the optical axis and outside of the optical axis. However, when it performs measurements outside of the optical axis, it does not control the focusing on the sample. When it performs measurements in the optical axis, it does not control the focusing and it measures only samples with very low curvature.

This invention is intended to overcome such a technical problem.

DESCRIPTION OF THE INVENTION

The invention relates to a device for measuring characterisation by reflectometry including a source that emits a light beam, a detector, means for processing and controlling this light beam so as to focus it on a reflective surface to be measured in the form of a spot and to receive it on said detector, command and acquisition means, a camera and means for imaging said spot on said detector and on said camera, characterised in that said camera is connected to the command and acquisition means so as to automatically focus the spot on the reflective surface to be measured and to automatically conjugate the reflective surface to be measured with the surface of the detector.

Advantageously, the surface of the spot is smaller than 5 mm².

The device of the invention enables the focusing of the incident beam to be controlled automatically on the surface to be measured and the surface of the sample and the surface of the receiver to be conjugated by image processing.

The invention enables a precise measurement to be obtained of an object located on the optical axis or near it, of a sample having a certain curvature.

In an advantageous embodiment, the focusing optics used in detection are oversized with respect to the focusing optics through which the incident beam passes.

Such an oversizing of the focusing optics enables greater curvatures to be measured than allowed by the spectrophotometer described in the document referenced [2], which has non-oversized receiving optics. The use of oversized optics makes it possible to have a larger numerical aperture and consequently better focusing precision with better control of the geometric scope.

Advantageously, the device of the invention can include a mobile support on which the sample is placed. The incident light beam can be emitted by a laser. The incident light beam can be transported by an optical fibre. The device of the invention can include separating cubes produced by optical fibre Y-junctions.

In an example of an embodiment, the device of the invention includes:
 a white light source having a strong directional luminance,
 an aspheric condenser,
 an achromatic focusing lens,
 a monochromator with a grating that can be blazed,
 a rotary disk,
 an optical system for achromatic collimation and a spatial filter,
 a filter wheel,
 a first separating cube, a reference channel that includes focusing optics, a photodiode connected to a command and acquisition processor, a sample channel that includes focusing optics, the sample mounted in an adjustable support via a connection using a protocol for communication by means of the processor, a second separating cube, a measuring channel that includes achromatic focusing optics, a detector connected to the processor, an imaging channel that includes achromatic focusing optics, a microscope objective, a camera connected to the processor.

The invention also relates to a process for measuring characterisation by reflectometry in which an incident light beam is processed and controlled so as to focus it on a reflective surface to be measured in the form of a spot and to receive it on a detector, in which said beam is imaged on said detector and on a camera, characterised in that the output data of said camera is acquired so as to automatically focus the spot on the reflective surface to be measured and to automatically conjugate the reflective surface to be measured with the surface of the detector.

Advantageously, the surface of said spot is smaller than 5 mm$^2$.

In an advantageous embodiment, focusing optics in detection, which are oversized with respect to the focusing optics through which the incident beam passes, are used.

This process can include the following steps:

activating the instruments, choosing the spectral parameters, positioning the sample, passing through all of the wavelengths λi, changing a variable i between 0 and N:

positioning a monochromator on the path of the incident beam at a wavelength λi so that λi=λ min+ixΔλ, positioning a suitable filter on the path of the incident beam, focusing the beam on the sample owing to the image processing, applying positional feedback control on the sample, acquiring signals for the measurement.

The device and process of the invention can be used in various fields such as the fields of metrology, colorimetry, control of optical systems, chemical and physical analyses, optical coding, and in various other fields in which it is necessary to study the quantities associated with light spectra.

The invention can thus be used for:

spectral control of optical systems, measuring the heterogeneity of samples because it enables local measurements of reflection at the surface of these samples to be obtained, which samples can be sheets, planar and non-planar mirrors for the optics industry or the like, characterising the reflection of samples with slight curves, on-site surface reflection measurement, with an adjustable optical head, using a portable apparatus, obtaining, with high precision, calorimetric data of the reflective surface, measuring shaped parts, adding the device of the invention in the form of a module in existing spectrophotometers, determining the diffusion (BRDF or "Bidirectionnal Reflectance Distribution Function") of an object with all of the applications associated with this type of measurement (control of pollution, roughness).

DETAILED DESCRIPTION OF SPECIFIC EMBODIMENTS

Below, to simplify the description, we will consider the reflective surface to be measured as the surface of a sample formed by an opaque reflector. However, this reflective surface to be measured can of course be the surface of an object, for example that of a vehicle body.

Figure 1:
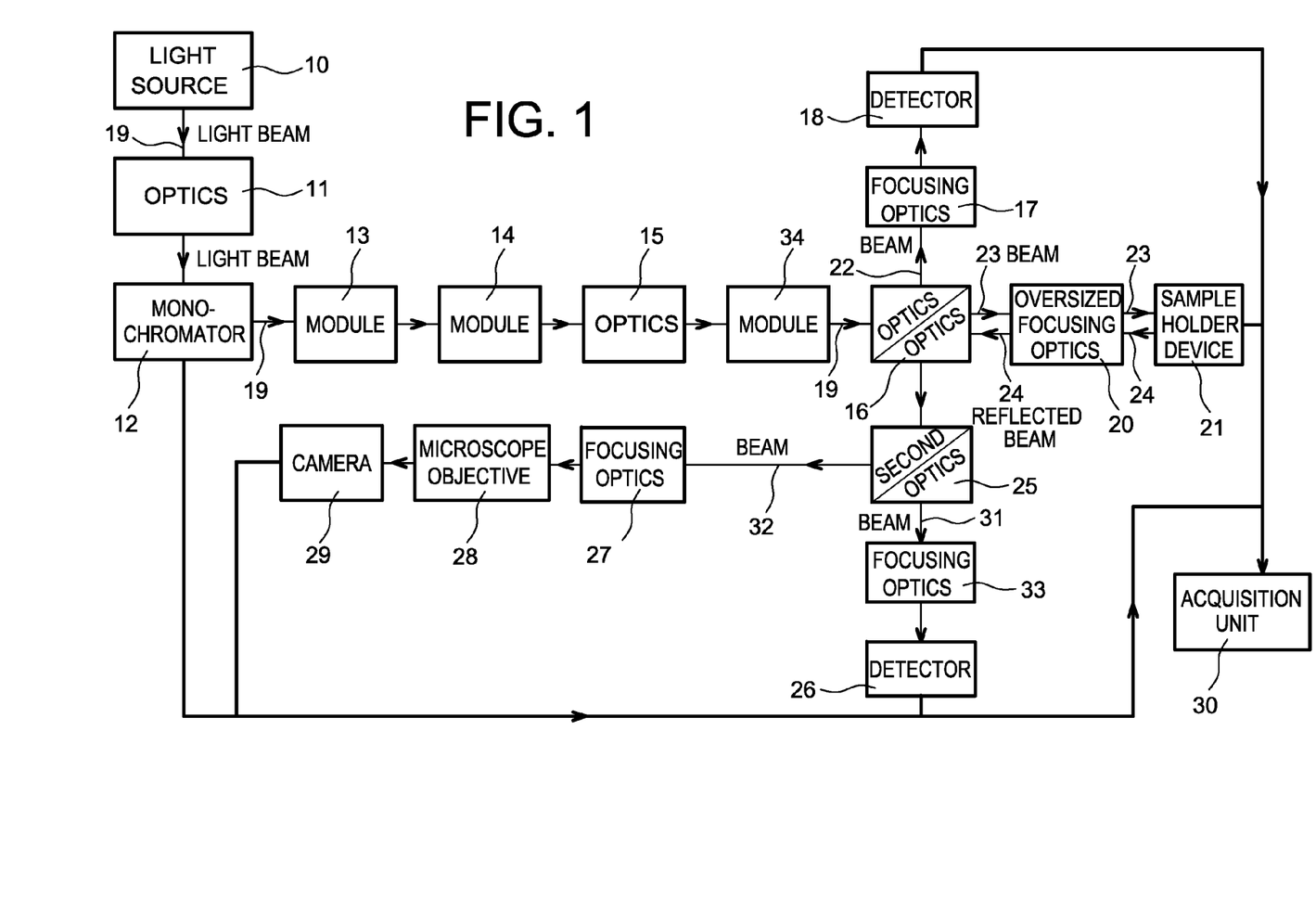
FIG. 1 shows the measuring device of the invention.

The device of the invention for measuring characterisation, shown in FIG. 1, includes:

an intense white light source 10 that emits a light beam 19, optics 11 for collecting and focusing said light beam 19, a monochromator 12, which is a system comprising a dispersive prism or grating element (which may or may not be blazed), which disperses the white light according to the wavelength and according to the various orders in the case of a grating, a module 13 for modulating the light beam, for example an opaque rotary disk having regular transparent openings for transmitting the light synchronously when the disk is moved by a rotation movement at constant speed, enabling the noise to be minimised owing to heterodyning, a module 14 for spatial filtering of this light beam, optics 15 for collimating this light beam, a module 34 for filtering this light beam, first separating optics 16 dividing the light beam 19 into two beams 22 and 23 corresponding respectively to a reference channel and the sample channel.

The measuring device of the invention also includes:

on the reference channel:

focusing optics (for example a lens) 17, and a detector 18, connected to a command and acquisition unit 30, enabling synchronous detection, on the sample channel:

oversized focusing optics 20, a sample holder device 21, which includes a mobile support on which a sample consisting of an opaque reflector is placed, and which returns a reflected beam 24 to the focusing optics 20, second optics 25 for separating this reflected beam 24 into two beams 31 and 32 corresponding respectively to a measuring channel and to an imaging channel, on the measuring channel, oversized focusing optics 33 and a detector 26, connected to the command and acquisition unit 30, enabling synchronous detection, on the imaging channel, oversized focusing optics 27 a microscope objective 28 and a camera 29 connected to the command and acquisition unit 30.

In this device, the beam 19 is focused on the surface to be measured, which in this case is the surface of a sample, in the form of a spot that is imaged on the detector 26 and on the camera 29, enabling automatic focusing of the image on said sample to be tested and conjugation of the sample surface and the detector surface. Such a feature advantageously enables the invention to be differentiated from the document referenced [2], in which only the incident flux is focused.

The surface of this spot on the sample is smaller than 5 mm², for example around 1 mm², enabling shaped parts to be measured. The reception focusing optics can be oversized with respect to the focusing optics through which the incident beam passes, enabling the incident beam to be maximally recovered when the angle of incidence is not zero. The use of oversized focusing optics makes it possible to have a greater numerical image aperture and therefore better focusing precision with better control of the geometric scope. These different features enable good precision in the specular reflection measurement.

Figure 2:
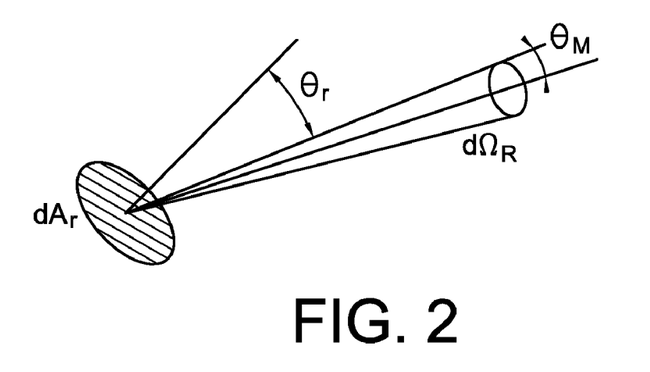
FIG. 2 shows the definition of the geometric scope.

Thus, the geometric scope seen by the receiver by conjugating the reflective surface of the sample (the object) and the receiver (the image) is preserved. The geometric scope ($d^2G$) is defined as being the product between the area of the receiver ($dA_r$), the cosine of the angle between the local normal to the receiver and the receiving direction ($\theta_R$), and the solid angle under which the source is seen ($d\Omega_R$), as shown in FIG. 2.

We thus have: $d^2G = dA_r \cdot \cos\theta_R \cdot d\Omega_R$

As the focusing and collimation optics are circular, there is a rotational symmetry about the optical axis. The geometric scope is then expressed, with $\theta_M$ the half-angle at the peak, by: $G = \pi \cdot A_r \cdot \sin^2\theta_M$. The optical scope defined by the ratio to the square of the index of the medium by the geometric scope is expressed, according to FIG. 3, for the object and image spaces of the optical and receiving system 35, which comprises an input pupil 36 and an outlet pupil 37.

Figure 3:
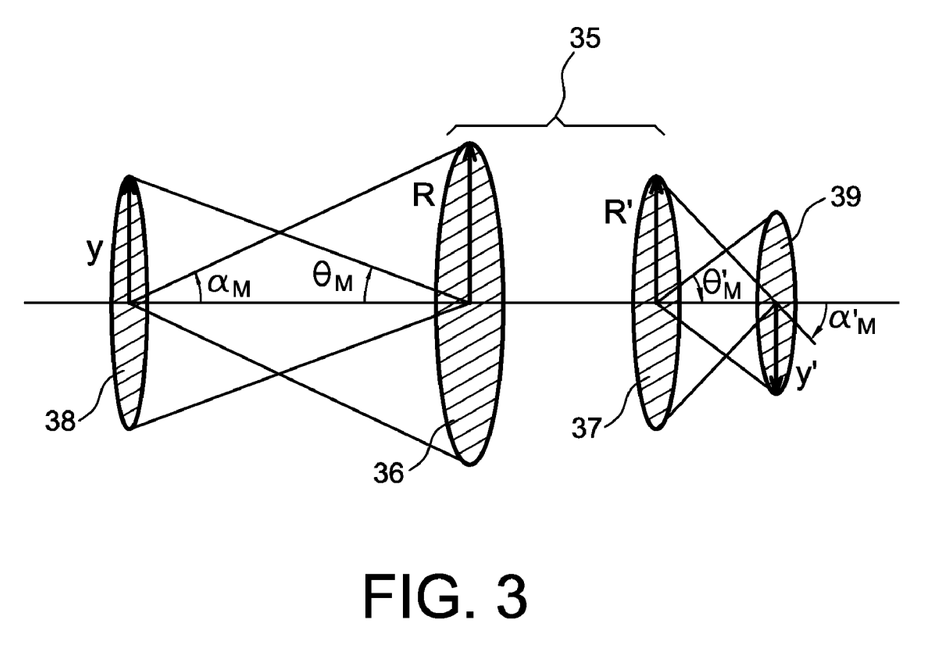
FIG. 3 shows the definition in the object space and in the image space of the geometric scope.

For the reflective object 38: $n^2 \cdot G = (\pi \cdot n \cdot R \cdot \sin\theta_M)^2$ For the detector image 39: $n'^2 \cdot G' = (\pi \cdot n' \cdot R' \cdot \sin\theta'_M)^2$.

If the system is aplanatic (small object located near the optical axis), the Abbe sine condition is respected, to have the following relation:

$$n \cdot y \cdot \sin\alpha_M = n \cdot R \cdot \sin\theta_M = n' \cdot R' \cdot \sin\theta'_M = n' \cdot y' \cdot \sin\alpha'_M$$

where n (n', respectively) is the object (image, respectively) medium index, y (y', respectively) is the height of the object (image, respectively), $\alpha_M$ is the half-angle at the peak under which the reflective sample sees the inlet pupil, $\alpha_{M'}$ is the half-angle at the peak under which the detector sees the outlet pupil, R is the radius of the inlet pupil 36, R' is the radius of the outlet pupil 37, $\theta_M$ is the half-angle at the peak under which the inlet pupil 36 sees the reflective sample 38, $\theta_{M'}$ is the half-angle at the peak under which the outlet pupil 37 sees the detector 39.

Thus, by preserving the field (y) and the aperture ($\alpha_M$) in the receiving optics system, by focusing, the entire reflected beam is captured by the detector 39. This focusing is performed, for each wavelength λi, automatically via a feedback control system by imaging. The camera 29 gives the image of the beam on the surface of the sample to be measured. The focusing is achieved owing to the repositioning of the sample 38 according to the optical axis, and can have, as a stopping criterion, the sharpness of the spot. However, other sopping criteria can be considered: for example, the image of a target or defects at the surface of the sample.

Figure 4A:
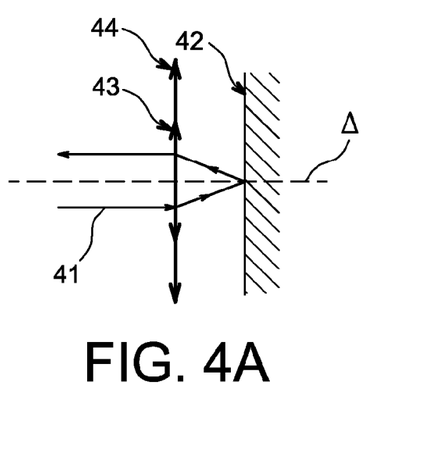
FIGS. 4A and 4B show the collective role of oversized focusing optics.
Figure 4B:
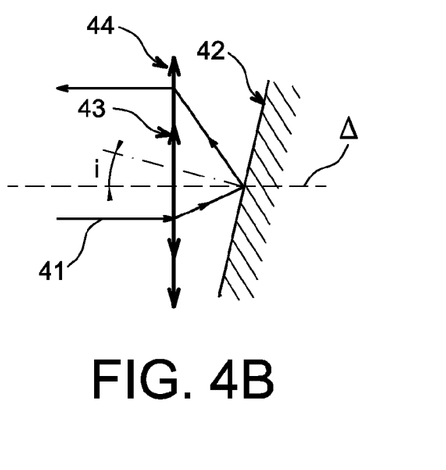

The choice of optics (materials, diameters, focal lengths) enables the costs and performance of the process to be more or less reduced. The source 10 must have the strongest spectral luminance possible and emit in a small cone. The initial light beam 19 has a diameter clearly smaller than the diameters of the focusing optics (lenses) and it is focused on the sample so as to have the smallest area possible, for example 1 mm². Thus, the light spot at the surface of the sample is clearly smaller than the spot of a conventional spectrophotometer. The oversizing of the focusing optics with respect to the size of the spot increases the angle of acceptance i of the reflected beam, as shown in FIGS. 4A and 4B: FIG. 4A shows the reflection of a beam 41 on a mirror 42 (reflective sample) with a lens 43, 25 mm in diameter, and with a lens 44, 50 mm in diameter, Δ being the optical axis. FIG. 4B shows the reflection of this same beam 41 on the same mirror 42 with a large angle of incidence i. The chromatic aberration is minimized by choosing achromatic lenses. The automation of the sample support also provides a possibility of mapping the sample in reflection in order to quantify the heterogeneities.

Figure 5:
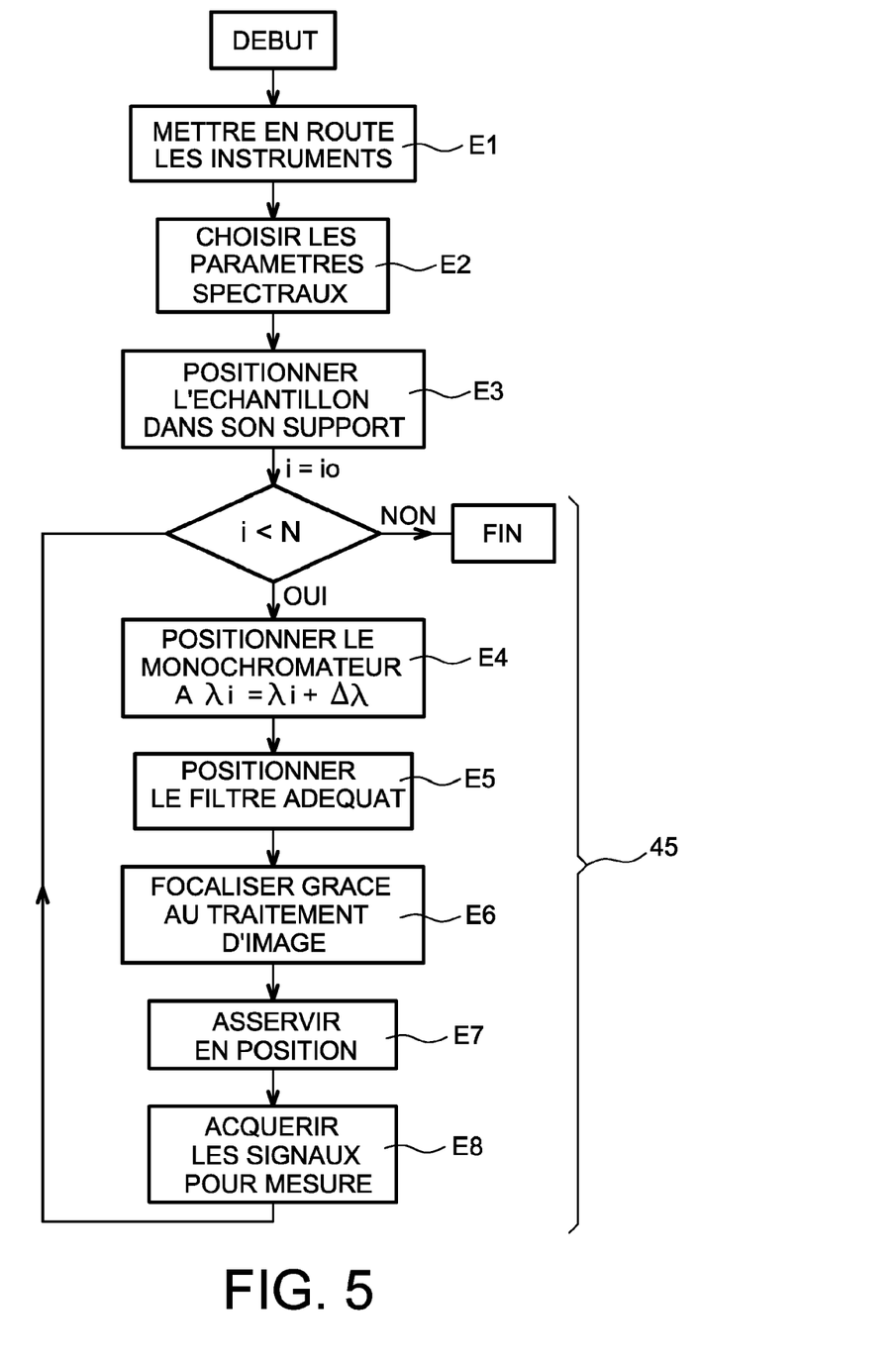
FIG. 5 shows the various steps of the process of the invention.

The process of the invention, shown in FIG. 5, includes the following steps:

activating the instruments: i.e. turning on the source, the detectors, and the test instruments (E1), choosing the spectral parameters: spectral range and resolution (E2), positioning the sample in its support (E3), passing through all of the wavelengths λi (or lambda i), changing a variable i between 0 and between 0 and N (loop 45):

positioning the monochromator 12 at a wavelength λi so that λi=λ min+ixΔλ (E4), positioning the appropriate filtering module 14 for example by positioning the modulation module 13 (E5), focusing the beam 24 on the sample owing to the image processing (E6), applying positional feedback control on the sample (E7), acquiring the signals for the measurement (E8).

Various alternative embodiments are possible:

The process of the invention can be applied to single-spectral studies with one or more laser-type light sources. It is possible to use, for example, an excimer laser in the ultraviolet, a HeNe laser in the visible, and a laser diode or any other laser in the near infrared.

The light source 10 may or may not be a fibre laser, white or emitting spectral rays.

The device of the invention can be produced with optical fibres. The separating cubes 16 and 25, for example, can be produced with chained optical fibre Y junctions.

The separating optics can be cubes, stages or any components separating the light into two more or less equal parts. However, to have the maximum flux on the measuring and image channels, 50/50 separators are advantageously used.

The focusing optics or a portion therefore can be replaced by suitable mirrors.

The device can be optimized by using additional powered translation stages, for example for moving the focusing optics of the imaging channel, in order to reduce the influence of residual chromatic aberrations.

It is possible for the sample support not to be automated in order to achieve the feedback control. The feedback control can be achieved by powered stages supporting the focusing optics. A stage can be added for feedback control of the position of the optical system with respect to the sample.

The device of the invention can be integrated into other spectrophotometers.

The criterion of focusing by positional feedback control may be dependent on any image processing: algorithms, target, surface defects, scratches, pin-holes, specific symmetry of the light beam, minimum image variation as a function of the angle of rotation of the sample.

The focusing can be manual and performed a single time at the beginning of acquisition, taking into account the offset of the optical system due to chromatic and geometric aberrations previously determined.

The device of the invention can be extended to diffusion measurements.

Example of an Embodiment

Figure 6:
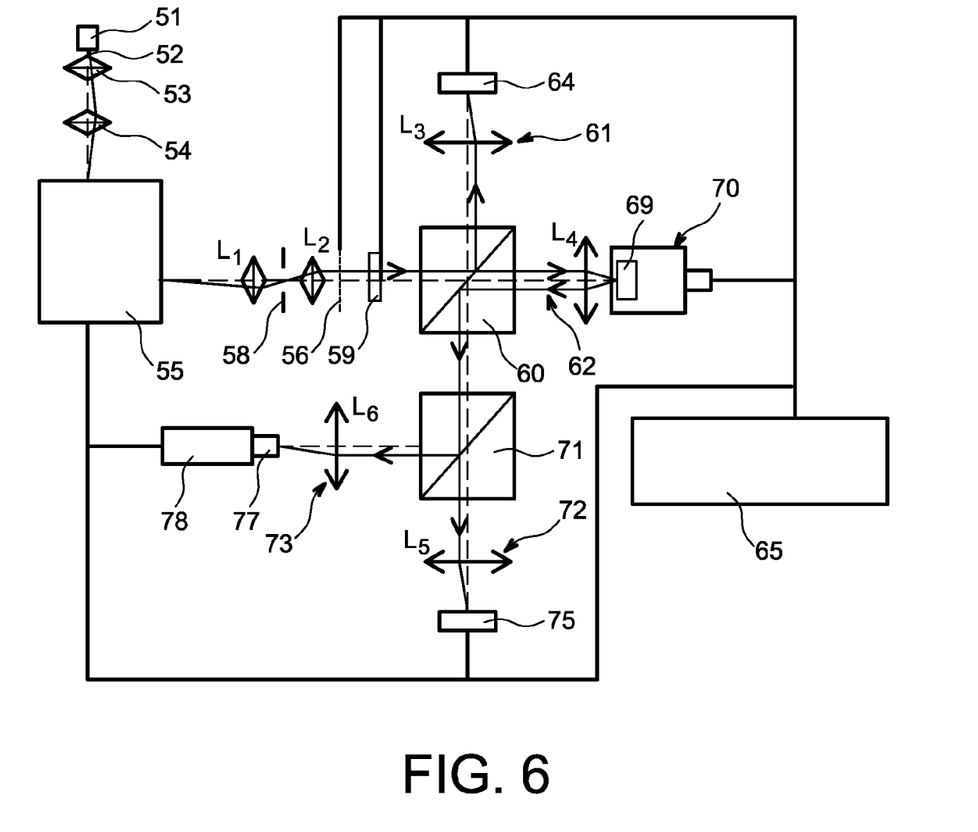
FIG. 6 shows an example of an embodiment of the device of the invention.

In an example of an embodiment, shown in FIG. 6, the device of the invention includes:

a white light source (halogen bulb) 51 with a strong directional luminance, which is injected into an optical fibre 52, with around 1 mm² of core surface and with a numerical aperture, for example, of 0.22, a condenser 53, which is an optical system with a short focal length with respect to its diameter, enabling it to collect a maximum amount of light owing to a larger solid receiving angle, aspherical, i.e. corrected of the spherical aberration; which condenser therefore collects maximum flux from the optical fibre 52, an achromatic focusing lens 54, which couples the energy in a monochromator 55 in accordance with its numerical aperture, the monochromator 55, which has a blazed grating (i.e. designed so as to disperse the maximum optical flux (in a single order, generally order 1) in the visible dispersing light, in which the choice of the grating used sets the spectral range and the fineness), a rotary disk 56, which modulates the light flow so as to filter the signal owing to a synchronous detection, in which the modulation frequency is optimized in order to minimize the optical and electronic noise present in the room, an achromatic optical collimation system (focusing optics L1, L2) and a spatial filter 58, for example a diaphragm, giving the dimension of the light spot on the sample, a filter wheel 59, which rejects the parasitic harmonic from the monochromator 55, which filter wheel is a mechanical system including four positions, in which a spectral filter is arranged on each of these positions in order to reject the parasitic harmonics of the dispersive element to be determined, in this case the monochromator, and which filter wheel can also be used to introduce neutral densities on the path of the light beam in order to prevent saturation of certain detectors (use of photomultiplier) when using an intense source, a first separating cube 60, for example with a 50-mm side, which divides the light beam into two parts; for the incident beam, the cube 60 separates the beam on the reference channel 61 and on the sample channel 62, and for the reflected beam it separates the measuring channel from a parasitic channel, the reference channel 61, which includes focusing optics L3, a photodiode 64 enabling synchronous detection, and connected to a command and acquisition processor 65, the sample channel 62, which includes focusing optics L4 produced with an aspherical condenser (reduction of spherical aberrations), for example, 50 mm in diameter, the sample 69, which is an opaque reflector, of which the transmission is zero, mounted in a support 70 adjustable according to two degrees of freedom (θ and φ) itself mounted on stages x, y powered via a connection using a communication protocol, for example IEEE, by means of the processor 65, a second separating cube 71, for example with a 50-mm side, which divides the reflected beam into a measuring channel 72 and an imaging channel 73, the measuring channel 72, which includes achromatic focusing optics L5, for example, 50 mm in diameter, a detector 75, enabling synchronous detection, connected to the processor 65, the imaging channel 73, which includes single achromatic focusing optics L6, for example 50 mm in diameter, a microscope objective (for example ×10) 77, a camera 78 connected to the processor 65.

In this example embodiment, the light source, which is white at the beginning, is spectrally resolved to obtain a quasi-monochromatic wave at the monochromator output. The beam is then spatially filtered by the spatial filter 58 located between the focusing optics L1 and L2, which is itself imaged at the surface of the reference photodiode 64 and the sample 69, then spatially separated by means of the first separating cube 60 toward the reference detector and toward the sample channel. The filter wheel 59 makes it possible to reject the higher orders from the monochromator 55. Then, a portion of the flux reflected by the sample is reflected onto the first separating cube 60 in order to again be spatially separated by the second separating cube 71 of which the transmitted channel is focused at the surface of the measuring detector 75, and the reflected channel imaged by the camera 78 is used for the feedback control of the focusing via the powered sample holder.

Figure 7A:
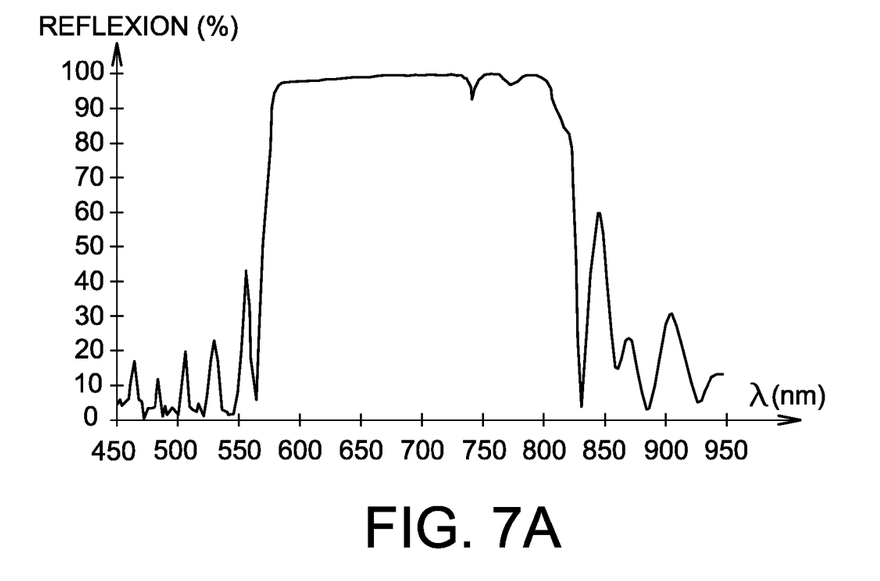
FIGS. 7A and 7B show the reflection as a function of the wavelength, respectively of a dielectric mirror (FIG. 7A), and a high-pass filter and a gold sample (FIG. 7B).

In FIG. 7A, the sample is a referenced dielectric mirror, which is formed by a stack of alternating bottom and top index oxide layers, which chose good spectral resolution. This mirror is a double mirror that has resonance peaks perfectly visible on the curve. The maximum level measured is around 100%, which corresponds to the maximum value of the reflection of this mirror (value measured on a low loss test set that evaluates the difference in flight time of a laser pulse of a cavity containing or not containing the mirror to be measured).

Figure 7B:
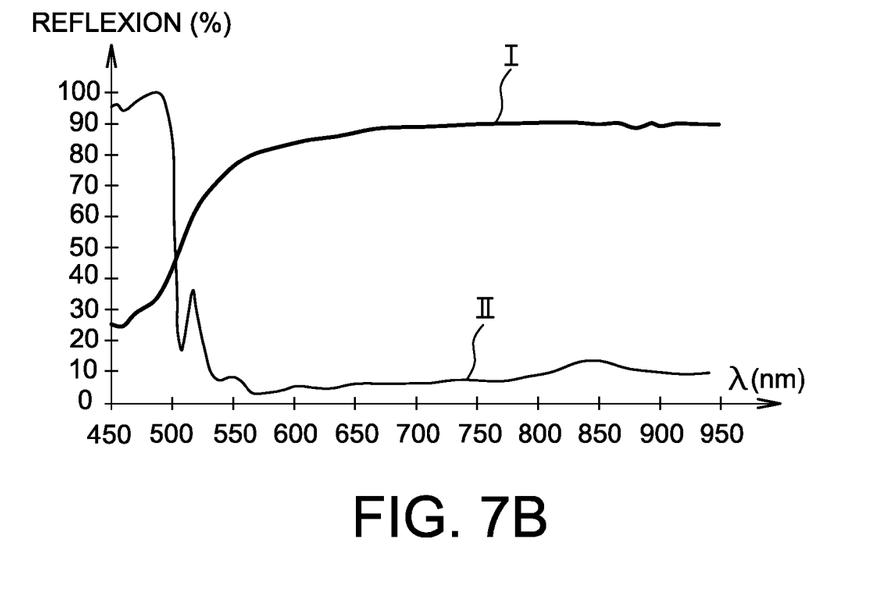

In FIG. 7B, the sample is a high-pass filter (curve II) or a gold sample (curve I).

Figure 8A:
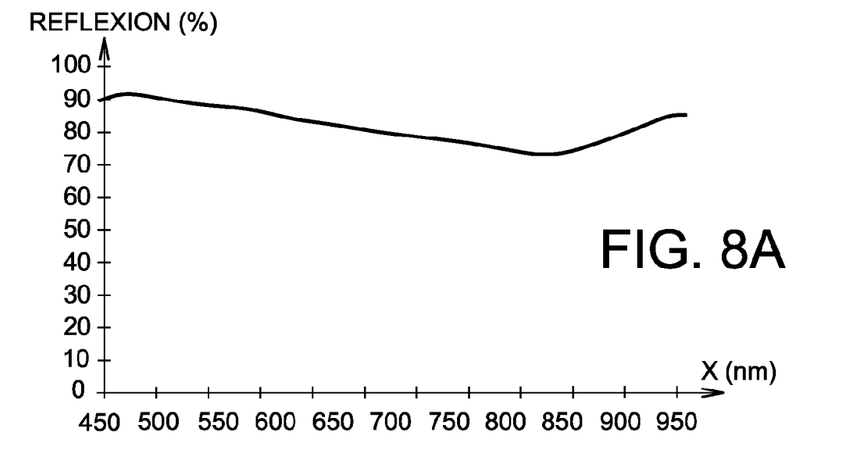
FIG. 8A shows the reflection as a function of the wavelength of a spherical mirror, shown in FIG. 8B.
Figure 8B:
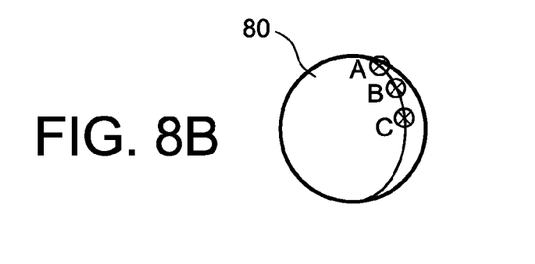

FIG. 8A shows the reflection as a function of the wavelength of a spherical mirror, shown in FIG. 8B, with a focal length of 160 mm and a diameter of 25 mm, having a maximum tilt angle of 4.4°. This figure shows the reflection coefficient for such a spherical mirror covered with an aluminium layer at three distinct measuring points A, B and C of its surface. The reflection coefficient is identical regardless of the wavelength. For these three points A, B and C, the curves are superimposed. In addition, we find the classic aluminium values obtained on a planar substrate (89% toward 500 nm) and the hollow is observed toward 850 nm. This measurement validates the device of the invention, which enables non-planar parts to be measured.

REFERENCE

[1] Patrick Bouchareine, "Spectrométrie Optique", Les Techniques de l'Ingénieur, Traité Mesures et Contrôle, R6310, pages 1 to 31, October 1994.

[2] D. Enard and H. Visser, "Universal spectrophotometer for determining the efficiency of optical components and systems", Applied Optics Vol. 21, No. 24, pages 4459-4464, 1982.

The invention claimed is:

1. Device for measuring characterization by reflectometry of a sample with a reflective surface which successively comprises:

a light source that emits a light beam, optics to collect and focus the light beam through the device, the optics image the light beam onto both the surface of the sample and onto at least one photodetector, a spectral or temporal disperser, spatial or temporal modules to filter the light beam in order to reduce an acquisition noise, a spectral or temporal separator to obtain two different signals, a focusing optics which is oversized compared with the light beam, a camera to visualize a spot image on the reflective surface of the sample, wherein the spectral or temporal disperser is a monochromator, wherein the acquisition noise is electronic noise, optical noise, or both, wherein the two different signals are a reference signal and a measurement signal that do not interfere, both signals being a reference channel and a sample channel, wherein at least one of the optics is large in size compared with the light beam, and wherein the at least one photodetector is connected to comment and acquisition units.

2. Device according to claim 1, wherein the reflective surface to be measured is the surface of a sample.

3. Device according to claim 1, wherein the surface of this spot is smaller than 5 mm$^2$.

4. Device according to claim 1, wherein the focusing optics used in detection are oversized with respect to the focusing optics through which the incident beam passes.

5. Device according to claim 2, wherein a mobile support on which the sample is placed.

6. Device according to claim 1, wherein the incident light beam is emitted by a laser.

7. Device according to claim 1, wherein the incident light beam is transported by an optical fibre.

8. Device according to claim 7, which includes separating cubes produced by optical fibre Y-junctions.

9. Device according to claim 1, which includes: an aspheric condenser, an achromatic focusing lens, a rotary disk, an optical system for achromatic collimation, a filter wheel, a first separating cube, a second separating cube, a measuring channel, which includes achromatic focusing optics, and a detector connected to the processor, an imaging channel, which includes achromatic focusing optics, a microscope objective, and a camera connected to the processor, wherein the sample, is mounted in an adjustable support via a connection using a protocol for communication by means of the processor, and wherein the monochromator has a grating that is a blazed grating.

10. Process for measuring characterisation by reflectometry wherein an incident light beam is processed and controlled so as to focus it on a reflective surface to be measured in the form of a spot and to receive it on a detector, wherein said beam is imaged on said detector and on a camera, characterised in that the output data of said camera is acquired so as to automatically focus the spot on the reflective surface to be measured and to automatically conjugate the reflective surface to be measured with the surface of the detector, wherein a reference signal and a measurement signal that do not interfere, are obtained by a spectral or temporal separator.

11. Process according to claim 10, wherein the reflective surface to be measured is the surface of a sample.

12. Process according to claim 10, wherein the surface of said spot is smaller than 5 mm$^2$.

13. Process according to claim 10, wherein focusing optics in detection, which are oversized with respect to the focusing optics through which the incident beam passes, are used.

14. Process according to claim 11, which includes the following steps: activating the instruments, choosing the spectral parameters, positioning the sample, passing through all of the wavelengths $\lambda i$, changing a variable i between 0 and N, positioning a monochromator on the path of the incident beam at a wavelength $\lambda i$ so that $\lambda i=\lambda min+ix\lambda$, positioning a suitable filter on the path of the incident beam, focusing the beam on the sample owing to the image processing, applying positional feedback control on the sample, and acquiring signals for the measurement.

* * * * *